US010107789B2

(12) United States Patent
Shanks et al.

(10) Patent No.: US 10,107,789 B2
(45) Date of Patent: Oct. 23, 2018

(54) MULTI-COMPONENT FLUID DETERMINATION IN A WELL BORE

(71) Applicant: Zenith Oilfield Technology Limited, Inverurie, Aberdeenshire (GB)

(72) Inventors: David Sirda Shanks, Aberdeen (GB); David Cyril Hendry, Aberdeenshire (GB); Alan James Fenwick, Aberdeen (GB)

(73) Assignee: ZENITH OILFIELD TECHNOLOGY LIMITED, Aberdeenshire (GB)

(*) Notice: Subject to any disclaimer, the term of this patent is extended or adjusted under 35 U.S.C. 154(b) by 19 days.

(21) Appl. No.: 14/775,352

(22) PCT Filed: Mar. 10, 2014

(86) PCT No.: PCT/GB2014/050693
§ 371 (c)(1),
(2) Date: Sep. 11, 2015

(87) PCT Pub. No.: WO2014/140539
PCT Pub. Date: Sep. 18, 2014

(65) Prior Publication Data
US 2016/0033468 A1 Feb. 4, 2016

(30) Foreign Application Priority Data
Mar. 11, 2013 (GB) .................................. 1304282.5

(51) Int. Cl.
*G01V 3/18* (2006.01)
*G01N 33/28* (2006.01)
*G01V 3/38* (2006.01)

(52) U.S. Cl.
CPC ........... *G01N 33/2823* (2013.01); *G01V 3/38* (2013.01)

(58) Field of Classification Search
CPC ...... G01N 33/2823; G01N 27/76; G01V 3/18; G01V 3/26; G01V 3/28; G01V 3/20;
(Continued)

(56) References Cited

U.S. PATENT DOCUMENTS 3,981,187 A 9/1976 Howell
4,267,727 A 5/1981 Hoppe
(Continued)

FOREIGN PATENT DOCUMENTS

CA 2323234 A1 4/2001
CN 1367858 A 9/2002
(Continued)

OTHER PUBLICATIONS

U.S. Appl. No. 14/346,863, filed Mar. 24, 2014, David Cyril Hendry et al.
(Continued)

*Primary Examiner* — Patrick Assouad
*Assistant Examiner* — Demetrius Pretlow
(74) *Attorney, Agent, or Firm* — GE Global Patent Operation (57) ABSTRACT

A fluid measurement system and method for determining component mixtures flowing in a conduit such as an oil well. The system includes a sensor wire for location in a well bore; a signal generator for injecting a high frequency signal along the wire; a data acquisition unit to record first reflected signals received from the wire; a system criteria unit to maintain a data set relevant to the system, and a processor unit operable to act upon the first reflected signals and the data set to establish an output indicative of component fluid within the well bore from which the mixture of fluids flowing within the well bore can be determined. An iterative process can be used with waveguide and probabilistic models.

20 Claims, 5 Drawing Sheets (58) Field of Classification Search
CPC . G01V 3/22; G01V 3/24; G01R 33/16; G01R 33/56536; G01R 33/34046; H01F 1/0018; H01F 1/062; H01L 21/76835; H01L 37/02; E21B 49/005; E21B 49/08; E21B 47/102; B01F 15/00227
USPC .............. 324/324, 325, 333, 338–343, 346, 324/355–356, 366–368
See application file for complete search history.

(56) References Cited

U.S. PATENT DOCUMENTS

| | | | |
|---|---|---|---|
| 4,429,273 A | 1/1984 | Mazzagatti | |
| 4,597,183 A | 7/1986 | Broding | |
| 4,909,855 A | 3/1990 | Burley | |
| 5,010,316 A | 4/1991 | Burley | |
| 5,025,222 A | 6/1991 | Scott et al. | |
| 5,030,294 A | 7/1991 | Burley | |
| 5,033,297 A | 7/1991 | Gustafson | |
| 5,132,903 A | 7/1992 | Sinclair | |
| 5,231,880 A | 8/1993 | Ward et al. | |
| 5,571,394 A | 11/1996 | Hettiarachchi et al. | |
| 5,818,241 A | 10/1998 | Kelly | |
| 5,926,024 A * | 7/1999 | Blount | G01N 22/00 324/324 |
| 6,064,002 A | 5/2000 | Hayami et al. | |
| 6,227,045 B1 | 5/2001 | Morse et al. | |
| 6,441,622 B1 | 8/2002 | Wrzesinski et al. | |
| 6,539,795 B1 | 4/2003 | Scherpenisse et al. | |
| 7,190,280 B2 | 3/2007 | Hall et al. | |
| 7,730,774 B2 | 6/2010 | Glasbergen et al. | |
| 7,900,699 B2 | 3/2011 | Ramos et al. | |
| 8,973,434 B2 | 3/2015 | Albrecht et al. | |
| 2003/0122535 A1 | 7/2003 | Williams et al. | |
| 2004/0031681 A1 | 2/2004 | Jett et al. | |
| 2004/0059513 A1 | 3/2004 | Bittar et al. | |
| 2004/0096614 A1 | 5/2004 | Quigley et al. | |
| 2005/0034873 A1 | 2/2005 | Coon et al. | |
| 2005/0083062 A1 | 4/2005 | Couch | |
| 2005/0172721 A1 | 8/2005 | Daigle | |
| 2005/0264302 A1* | 12/2005 | Mohajer | G01N 22/00 324/639 |
| 2005/0265121 A1 | 12/2005 | Scott | |
| 2005/0274513 A1 | 12/2005 | Schultz et al. | |
| 2006/0214098 A1 | 9/2006 | Ramos | |
| 2007/0071612 A1 | 3/2007 | Yuratich | |
| 2007/0119244 A1 | 5/2007 | Goodwin et al. | |
| 2007/0125163 A1 | 6/2007 | Dria et al. | |
| 2007/0158064 A1 | 7/2007 | Pribnow et al. | |
| 2007/0239360 A1 | 10/2007 | Rabinovich et al. | |
| 2008/0048669 A1 | 2/2008 | Scherber et al. | |
| 2008/0061789 A1 | 3/2008 | Coates et al. | |
| 2008/0083273 A1 | 4/2008 | Sroka et al. | |
| 2008/0111551 A1* | 5/2008 | Freedman | G01V 8/02 324/324 |
| 2008/1085138 | 8/2008 | Hernandez-Solis et al. | |
| 2008/0224705 A1 | 9/2008 | Simon et al. | |
| 2008/0317095 A1 | 12/2008 | Hadley et al. | |
| 2009/0277629 A1 | 11/2009 | Mendez et al. | |
| 2009/0326826 A1 | 12/2009 | Hull et al. | |
| 2010/0223011 A1 | 9/2010 | Parsche | |
| 2010/0254650 A1 | 10/2010 | Rambow | |
| 2011/0007776 A1 | 1/2011 | Yamamoto | |
| 2011/0081256 A1* | 4/2011 | Thompson | E21B 47/042 417/53 |
| 2011/0188344 A1 | 8/2011 | Hartog et al. | |
| 2011/0311179 A1 | 12/2011 | Greenaway | |
| 2012/0055253 A1* | 3/2012 | Sinha | G01N 29/024 73/622 |
| 2012/0075951 A1 | 3/2012 | Johnson et al. | |
| 2012/0186873 A1* | 7/2012 | Shayegi | E21B 44/00 175/25 |
| 2013/0091942 A1 | 4/2013 | Samson et al. | |
| 2014/0069810 A1 | 3/2014 | Tachibana et al. | |
| 2014/0290335 A1 | 10/2014 | Shanks | |
| 2015/0090040 A1 | 4/2015 | Schumacher et al. | |
| 2015/0233211 A1 | 8/2015 | Bujold et al. | |

FOREIGN PATENT DOCUMENTS

| | | |
|---|---|---|
| CN | 1723332 A | 1/2006 |
| CN | 2900784 Y | 5/2007 |
| CN | 101598581 A | 12/2009 |
| CN | 201396147 Y | 2/2010 |
| DE | 2521411 A1 | 11/1976 |
| DE | 19950111 C1 | 2/2001 |
| DE | 10052922 A1 | 5/2002 |
| EP | 0508894 A1 | 10/1992 |
| EP | 1098197 A2 | 5/2001 |
| EP | 1574853 A1 | 9/2005 |
| EP | 1662274 A1 | 5/2006 |
| GB | 2159663 A | 12/1985 |
| GB | 2246866 A | 2/1992 |
| GB | 2467177 A | 7/2010 |
| GB | 2484990 A | 5/2012 |
| WO | 9100996 A1 | 1/1991 |
| WO | 200011317 A1 | 3/2000 |
| WO | 2007109772 A2 | 9/2007 |
| WO | 2011044023 A2 | 4/2011 |
| WO | 2012052764 A1 | 4/2012 |
| WO | 2013045913 A2 | 4/2013 |

OTHER PUBLICATIONS

Kane et al., "Applications of time domain reflectometry to landslide and slope monitoring", TOR 2002—Second International Symposium and Workshop on Time Domain Reflectometry for Innovative Geotechnical Application, pp. 1-14, Dec. 31, 2001.

Jie et al., "Introduction to Numerical Simulation of Electrical Logging and Its Development Trend", Well Logging Technology, vol. No. 34, Issue No. 1, pp. 1-5, Feb. 28, 2010.

Combined Search and Examination Report issued in connection with related GB Application No. GB1116855.6 dated Dec. 15, 2011.

International Search Report and Written Opinion issued in connection with related PCT Application No. PCT/GB2012/052373, dated Jul. 12, 2013.

Office Action issued in connection with related EP Application No. 12779140.8-1605 dated Jul. 31, 2015.

Non-Final Rejection towards related U.S. Appl. No. 14/346,863 dated Oct. 29, 2015.

Unofficial English translation of Office Action issued in connection with related CN Application No. 201280048170.6 dated Dec. 29, 2015.

Notice of Allowance issued in connection with related U.S. Appl. No. 14/346,863 dated Apr. 19, 2016.

GB Search Report issued in connection with corresponding Application No. GB1304282.5 dated Jul. 25, 2013.

PCT Search Report and Written Opinion issued in connection with corresponding Application No. PCT/GB2014/050693 dated Jun. 27, 2014.

* cited by examiner

MULTI-COMPONENT FLUID DETERMINATION IN A WELL BORE

CROSS-REFERENCE TO RELATED APPLICATIONS

This is a national stage application under 35 U.S.C. § 371(c) of prior filed, co-pending PCT application serial number PCT/GB2014/050693, filed on Mar. 10, 2014, which claims priority to Great Britain Patent Application Serial No. 1304282.5 filed Mar. 11, 2013 and titled MULTI-COMPONENT FLUID DETERMINATION IN A WELL BORE. The above-listed applications are herein incorporated by reference.

BACKGROUND OF THE INVENTION

Embodiments of the invention relate to a method for determining the composition of a fluid mixture in a well bore and more particularly, to a method for improving the determination of the composition of a flowing fluid mixture along a length of a well bore.

The oil and gas industry is very dependent on well bore measuring techniques to provide information about what is actually happening deep in a well bore. Many surveys are done before oil or gas is produced, including seismic and rock porosity, water content and micro seismic. However, there are few methods of obtaining data which gives a broad measurement of the behaviour of the well over its whole length, especially while the well is being produced.

Point pressure and temperature sensors have been in commonplace use since the 1940's and production logging tools are also now customarily used. It is quite common in the oil and gas industry to run logging tools which measure water cut and well bore resistivity, and also optical distributed temperature sensing systems into oil wells to measure the temperature profile over the complete length of the well bore.

The point sensors only provide indications of what is happening at the position of the sensor. Logging tools measure the complete well bore, but not in real time and they can only be run periodically. Logging tools are also difficult to run, when there are pumps in the well bore. Distributed temperature measurement is limited by the fact that, while the temperature profile can be interpreted to give information about other behaviour in the well bore, the temperature information in its raw state is not immediately useful in terms of determining the type of fluid produced (or injected).

The oil and gas industry is under pressure to achieve greater efficiency and increase production rates, all of which requires more understanding of reservoir storage and production behaviour. This has created a need for more two dimensional and three dimensional measurements of reservoir behaviour.

SUMMARY OF THE INVENTION

Transmission lines are known for measuring interfaces between fluids by determining that a change in the dielectric properties between the transmission lines has occurred. This technique can be used to determine fluid levels in static, non-flowing, well bores as described in WO2011/044023 to Chevron USA Inc. WO2011/044023 discloses a system which includes a pulse generator to generate a pulse of electromagnetic energy to propagate along the wellbore towards a surface of the fluid, a detector to detect a portion of the electromagnetic pulse reflected from the surface of the fluid and propagated along the wellbore towards the detector, a processor to analyse detected signals to determine a level of the surface of the fluid. In an embodiment, the system includes a pump controller to control the operation of a pump located in the wellbore based on the fluid surface level. This technique can be used to determine fluid levels in static, non-flowing, well bores.

A disadvantage in this system is in the number of unwanted reflections which are present giving false readings. These reflections occur at any dielectric interface through the well bore so in a static well or if you are only looking for the fluid surface a simple reflection can be obtained. If you study a moving production zone such as across the perforated zone in a producing well the responses will contain many reflections in no particular order and also many gradual changing conditions so a simple reflection approach will not give good results.

To overcome this disadvantage the system proposes markers to give reflections at known depths to assist in determining the true reflection from the fluid surface. These may take the form of a coaxial choke or wiper arm which provide a local reduction in the dielectric properties over the length of the marker. Unfortunately, such markers do not work. This is because a reflection will occur when the pulse reaches the marker and when the pulse exits the marker due to the change in dielectric properties between the marker and the fluid. Each reflection will provide a response being the precise inverse of the other and, over the short length of marker, the responses will cancel each other out.

To also overcome the problems of unwanted reflections, the system provides an embodiment using a spooled pair of conductors as may be run into the well bore as part of a dewatering system. A disadvantage of this system is in the long cable lengths used to access deep wells where the pump is located. As the pulse generator is located at the surface, the pulse will have dispersed and reduced in signal strength by the time it has traveled to the fluid surface level it is supposed to measure. The same effects will occur on the reflected signal, which will, by its very nature of being a reflected response, be of reduced signal strength. If the system includes markers or a second fluid level is required to be determined, in practise, the return responses are indistinct at the surface of the well bore.

In WO2012/052764 the present Applicant's use of reference cable assemblies to remove the changes and effects of the well bore and installation, as well as recording reflection times of pulses, is described to improve the determination of the level of the surface of the fluid.

However, in this arrangement unwanted reflections still occur which give false readings. These reflections occur at any dielectric interface through the well bore and as the transmission line is created from the casing together with tubing located within the casing, acting as a central conductor, all connection points such as the casing joints will provide unwanted reflections and these can cause inaccuracy in the measurements made. In addition, it is not possible from either of these two existing methods to create a measurement of the fluid type in two dimensions over the well bore length. So in a producing well where fluids are moving and discrete water levels do not exist, or in a pumped well below the intake of the pump where the fluid enters the well bore from the formation, a continuous and varying mixture of fluids and gasses generally exists. The current technology therefore does not allow measurement of moving and variable fluid mixtures.

It is therefore an object of the present invention to provide a system and method of determining the fluid type and mixture present in a moving fluid over a length of a well bore.

According to a first aspect of the present invention there is provided a fluid measurement system comprising an elongate member for location in a well bore, a signal generator for injecting a high frequency signal along the member; and a data acquisition unit to record first reflected signals received from the member; a system criteria unit to maintain a data set relevant to the system, and a processor unit operable to act upon the first reflected signals and the data set to establish an output indicative of component fluid within the well bore from which the mixture of fluids flowing within the well bore can be determined.

The elongate member is a cable. The cable may be as used in level sensing systems and take the form of a sensor wire. There may be a plurality of sensor wires to provide alternative paths for the signal through the same volume of fluid. The sensor wires may be arranged in parallel and/or be twisted or spiraled together. The sensor wires may be of different lengths. The sensor wires may be arranged to branch from a first wire.

It has been found from experimental data that the characteristic impedance of such level sensing system cables varies depending on the fluid surrounding the cable. The precise mechanism being that the signal velocity, group and phase vary depending on the dielectric and conductive properties of the fluids. This in turn means the velocity of propagation changes depending on the fluid the cable is immersed in. The velocity in gas is the fastest, oil slower and water slower still. Therefore the time taken for a signal to reach the bottom of the cable and be recorded at surface is a measure of the composition of the fluids it has passed through. So if a cable was installed across an oil gas or oil water boundary or indeed in a moving mixture of oil and gas or oil and water the average velocity of propagation is a measure of the mixture of the fluids over the length of that cable sensor.

Such a system as detailed above, enables predetermined criteria to be used in conjunction with real time recorded data received from the member to determine the mix of fluids flowing in a well bore. By recording reflections created by inputting a high frequency signal along the member and acting upon these along with data such as structural knowledge of the well bore, waveguide theory knowledge and dielectric properties of fluids likely to be found in the well bore, an output indicative of the fluid mix in the well can be determined as in a more complex fluid mix environment, all significant fluid changes create reflections. In addition, all reflections which are not created by the lower end of the cable or member also cause multiple reflections, which also form part of the received reflected signals thus providing complex data indicative of the fluid mixture. Thus this signal response is complex containing many reflections and gentle distortions from gradual variations in the fluid mixture.

The signal generator is a high frequency signal generator providing a signal with a fast rise time, typically <5 nS. The signal may be selected from a group comprising: modulated carriers, pulse streams, pulse sequences, swept frequency sine waves and shorter simpler pulse bursts.

The signal generator may be operable to apply a second high frequency signal to the member and the data acquisition unit is operable to record second reflected signals received from the member; wherein the processor unit is operable to act upon the first reflected signals, second reflected signals and the data set to establish an output indicative of component fluid within the well bore from which the mixture of fluids flowing within the well bore can be determined.

By utilising a first signal and second signal and thus the first reflected signals and second reflected signals, a more accurate determination of fluid mix can be established.

Conveniently the first signal and second signal are different signals. By applying different signals, the differences in the received first and second reflected signals can be identified.

The first and second signals are identical signals and an alternative known differential is applied to the system. The use of a known differential enables the first and second reflected signals to be identified suitably.

Conveniently, the known differential is a time delay occurring between the first signal and second signal being applied to the member. The occurrence of a time delay enables constants within the bore to be easily identified and the mixture of fluids to be determined effectively.

The member may be provided with at least one adaptive unit. The adaptive unit may alter characteristics of the member. By adapting the characteristics of the member in a known manner, quantifiable known changes in reflected signals can be created thus giving a known reference. The first signal may be applied to the member before adaption and the second signal may be applied to the member after adaption to provide first reflective signals and second reflected signals with known variations in response. Creating such known variations in response within the reflected signals enables constant factors such as environmental factors to be identified and utilised in determining the mix of fluids flowing in the bore.

The local adaptive units may be electronics which act upon the member to alter termination resistance of the member. Such alteration of the termination resistance can create known variations in responses seen in the reflected signals.

The system may further comprise a plurality of signal generators located along the length of the member each having an associated data acquisition unit, each signal generator operable to inject signals into a section of the member thus increasing sensitivity of each acquisition unit in determining reflections occurring in the associated section of the member. Such an arrangement enables more small fluid mix changes to be identified more effectively.

The signal comprises a pseudo noise (PN) sequence of high frequency pulses. This removes the major problem of extracting valid reflections from other responses and noise from the cable system. If a PN sequence of high frequency pulses is transmitted instead of a single pulse and the response from the system is then compared looking for the correct pulse sequence, the resolution and potential cable depth which can be measured increases.

The system criteria unit data set includes a mathematical model of the well bore as well as a model of multiple fluid interfaces and multiple reflections from these fluid changes based on waveguide theory which can be modified taking into account the well bore environment in question and may also include an iteratively generated model of relevant environmental factors. The data set may further include a probabilistic model of possible fluid regimes which may occur in the well bore to further enhance the diagnosis of the complex data responses thus provide an output representative of a complex mix of fluid which may occur in the well bore.

Where PN sequence signal sources are used these can run both real time and continuously in parallel. Orthogonal PN sequences may be used so that two or more pulse sequences do not interfere with one another.

According to a second aspect of the present invention there is provided a method of determining a fluid mixture flowing in a conduit, the method comprising the steps: locating a first cable through a length of the conduit; injecting a first high frequency signal along the cable; recording a first response of reflected signals from the cable; utilising known conduit criteria and the first reflected signals to establish fluid characteristics; and determining a mixture of fluids flowing through the length of the conduit using the established fluid characteristics.

Changes and interfaces within the mixed fluid each cause reflections of the injected signal which provide data that can be used to determine the location and type of the interfaces and mixes thus by recording reflected signals and processing these in combination with known criteria relating to the conduit, the characteristics of the fluid flowing in the conduit can be determined.

The method is an iterative process. In this way the steps are repeated to improve the determination.

The method further comprises applying a second high frequency signal to the cable and recording a second response of reflected signals.

The second high frequency signal is applied to the cable a predetermined time period after the first high frequency signal is applied to the cable. This enables a predetermined known criteria to be applied in determining the first response and second response.

The method may further comprise the step of adapting the cable after the application of the first signal. Such a step would involve adapting the cable in a manner which creates known variations in response such that the first response and second response can be clearly identified from one another.

Step (b) comprises injecting a PN sequence of high frequency pulses and step (c) includes matching the correct pulse sequence to record a response.

Step (c) includes the step of comparing the response to a predetermined data set. The predetermined data set may be a mathematical model. The data set may include a mathematical model of the well bore as well as a model of multiple fluid interfaces and multiple reflections from these fluid changes based on waveguide theory which can be modified taking into account the well bore environment in question and may also include an iteratively generated model of relevant environmental factors. The data set may further include a probabilistic model of possible fluid regimes which may occur in the well bore to further enhance the diagnosis of the complex data responses thus provide an output representative of a complex mix of fluid which may occur in the well bore. More particularly, step (c) is repeated in an iterative process.

The method may also interpret a response by comparison to other responses.

The method includes the step of measuring responses at a plurality of locations along the cable. The responses may be measured at each end of the cable. The method may also include the step of generating signals at different positions along the cable. This allows determination over sections of the cable. Additionally, orthogonal PN sequences can be injected to avoid interference.

The method may include the step of measuring responses from a plurality of cables arranged through conduit.

The conduit is a well bore. Alternatively, the conduit is a pipe-line.

BRIEF DESCRIPTION OF THE DRAWINGS

Embodiments of the present invention will now be described, by way of example only, with reference to the accompanying drawings of which.

DETAILED DESCRIPTION

Figure 1:
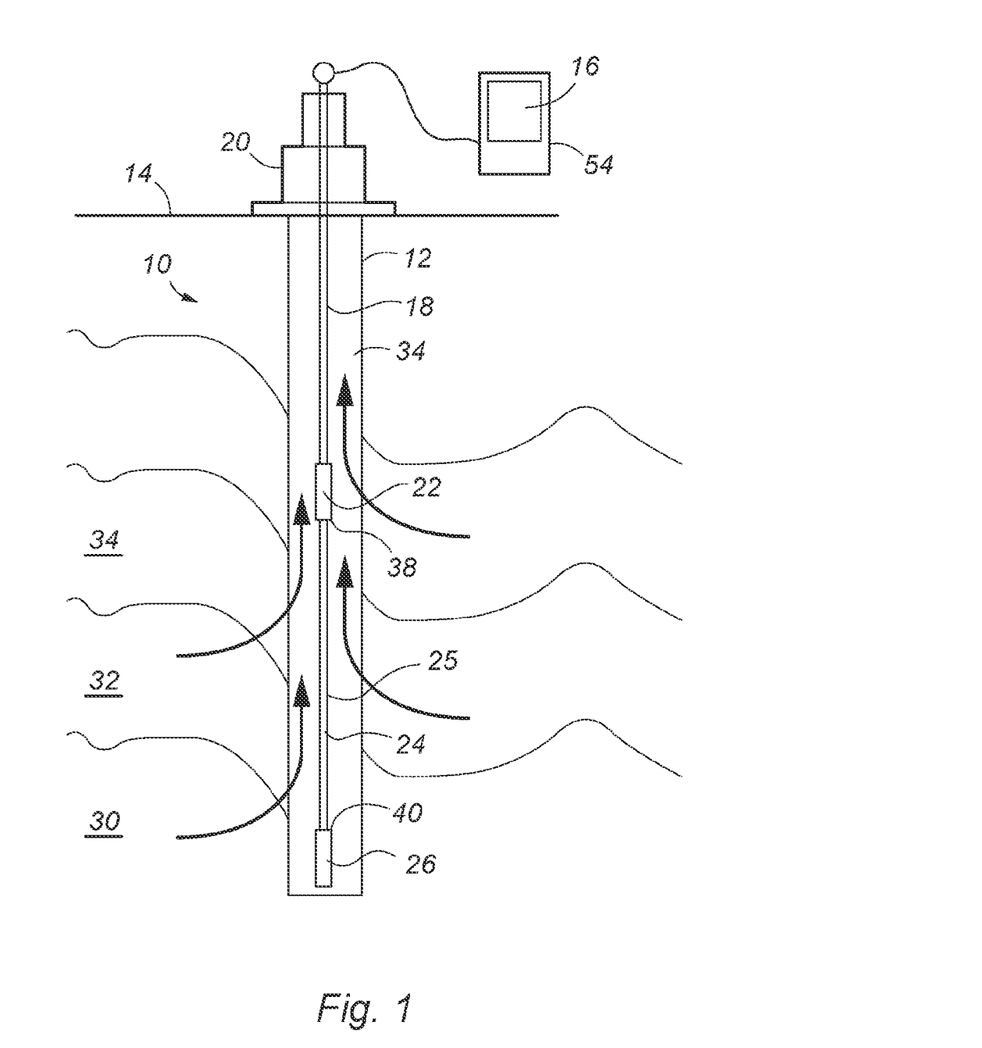
FIG. 1 is a schematic illustration of a fluid measurement system according to a first embodiment of the present invention.

Reference is initially made to FIG. 1 of the drawings which illustrates a fluid measurement system, generally indicated by reference numeral 10, according to an embodiment of the present invention. System 10 is located in a well bore 12. At the surface 14 of the well bore 12, is a processor based surface panel 16 for data acquisition, storage of system criteria and control of the system 10. The panel 16 is connected to a connecting cable 18 which runs through the wellhead 20 to access the well bore 12. The connecting cable 18 meets an upper electronics module 22 from which descends a sensor wire 24 terminating at a lower electronics module 26. Sensor wire 24 acts as the propagating section 25 for the fluid measurement system 10.

Well bore 12 is drilled in a geological formation 28 to access hydrocarbons in the form of gas 30 and oil 34. The hydrocarbons 30,34 will travel up the well bore 12 as a fluid mix 36 which typically includes brine/water 32. The fluid 36 flow can be natural if sufficient downhole pressure exists or alternatively, the fluid 36 is assisted to the surface typically by pumps (not shown) located in the well bore 12. The components and the quantities of each within the fluid mix 36 will vary as the fluid mix flows up the well bore 12 due to the entrance of further components along the length of the well bore. Additionally, components may combine to form multi-phase mixes with the presence of each pure component being dependent on the temperature and pressure at the respective location in the well bore 12. In order to produce the well bore 12 efficiently it is desired to know the composition of the fluid mix 36 with time and depth in the well bore 12.

The sensor wire 24 is entirely surrounded by the fluid mix 36. A high frequency pulse, typically with a rise time of <5 ns, is injected through the wire 24. The signal can be generated at the surface 16 or at the upper and/or lower electronics modules 22,26. The response to the pulse from the wire is detected at the electronics modules 22,26 and is typically a series of responses which have been reflected back to the source emitter.

It has been found from experimental data that the characteristic impedance of the wire 24 varies depending on the fluid surrounding the wire 24. The precise mechanism being that the signal velocity, group and phase vary depending on the dielectric and conductive properties of the fluids. This in turn means the velocity of propagation changes depending on the fluid the cable is immersed in. The velocity in gas is the fastest, oil slower and water slower still. Therefore the time taken for a signal to reach the bottom of the cable and be recorded at surface is a measure of the composition of the fluids it has passed through. A typical response to a pulse through a sensor wire 24, for oil 34, brine (salt water) 32 and gas 30 is shown in FIG. 2.

Figure 2:
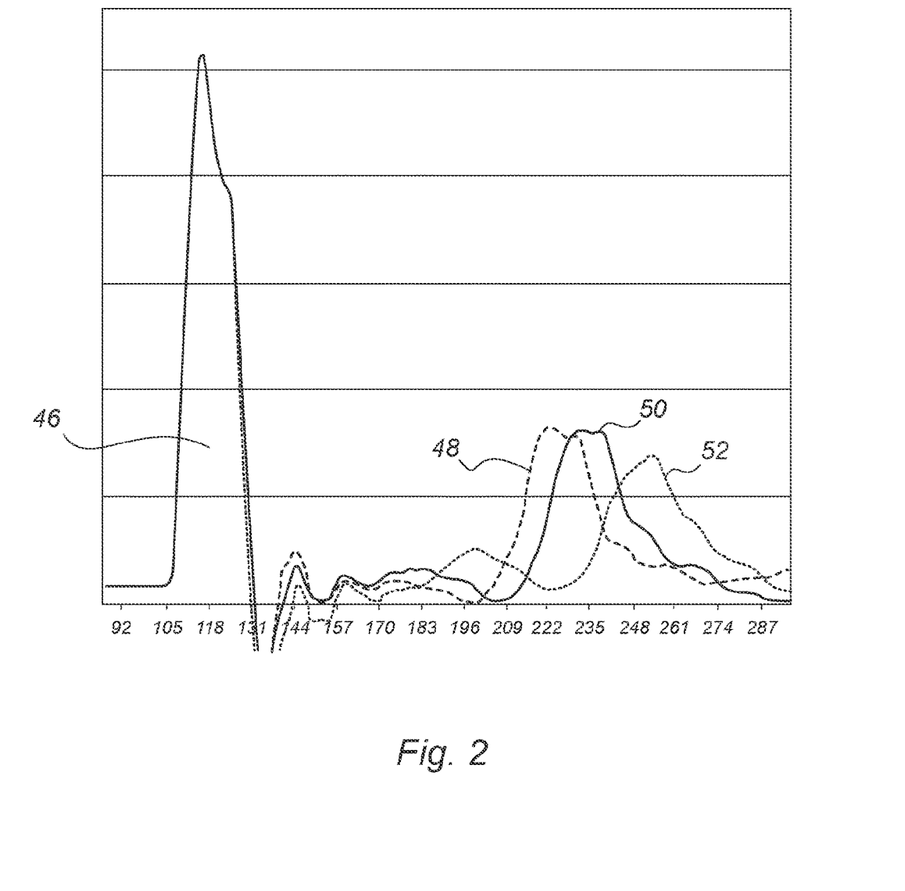
FIG. 2 is a graph of signal strength against time, illustrating the response for three pulses injected into gas, water and oil respectively.

Referring now to FIG. 2 there is shown a plot of signal strength 42 against time 44 which illustrates the basic principle that the velocity of the pulse as can be measured by the time for the reflection to return to the injection point, varies proportionally with the fluid type. The injected high frequency pulse 46 is injected into the sensor wire 24 from the upper 22 or lower 26 electronics module. The pulse is reflected at a boundary which in this simplistic case is the end of the propagation section 25 and returns to the source some time later. The time taken to return is proportional to the fluid mixture in the sensing zone which is the zone surrounding the propagation section 25. As seen in FIG. 2, the response pulse differs in time with the fastest being for a wire 24 surrounded by gas 48, then oil 50 and finally brine or salt water 52.

In use, in the arrangement of FIG. 1, a high frequency pulse or pulses which may for example be a pseudo noise sequences, chirp or other waveforms is injected into the down-hole sensor wire 24 and the responses received will include reflections from fluid interfaces, known features of the cable, such as markers and imperfections, interactions with the liner of the bore and the terminating impedance. It will be appreciated that in this embodiment, local down hole electronics can be used to measure the response of the sensor cable to the input from both ends of the sensor cable.

The response is detected in a data acquisition unit 54 housed in an electronics module 22,26 or in the surface processor 16. The response is then analysed in combination with system criteria data to determine the components of the fluid mixture 36.

The system criteria data utilised in this process includes data acquired by measuring the exact RF behaviour of the chosen sensor wire in the exact well bore conditions expected, such as pipe diameter and also sample fluids. The measurements may include, although not exclusively include, measurable quantities such as pulse transmission speed and characteristic impedance.

In addition, the system criteria data may further include all known information about the well bore the Sensor wire 24 is suspended in such as depth and pipe or bore hole diameter, and previously measured dielectric properties of all fluids potentially present, such oils brine and gas as discussed above.

The system data criteria can further include data generated using waveguide theory wherein a mathematical model can be created which can predict the pulse velocity and the amplitude and polarity of any reflection of the injected pulse, or stream of pulses, when it meets any marker, termination or change in fluid or gas mixture.

It will be appreciated that as the injected signal is input into the Sensor wire 24, all non-terminal reflective interfaces are likely to cause multiple reflection, for instance, where there is a reflection from a water interface beyond an impedance marker, which then is reflected from the marker on its return to the pulse source, and then rebounds back and forth producing a small and decaying in time, pulse response at each rebound. Therefore to increase the accuracy of composition data output from the system, the waveguide based model can be extended to accommodate and process multiple reflection and rebounds from fluid interfaces.

In addition to the processor utilising the measured system criteria data and waveguide model, a probabilistic model which includes all possible combinations of fluids and is able to attach probability to the likelihood of any given fluid combination scenario being present can also be developed.

This probabilistic model can be utilised by the processor unit in combination with the waveguide model and received response to provide an output reflective of the composition of the fluid in the well bore.

To determine the composition data output, the processor unit will process the recovered data extracting the largest and most prominent responses first and iterate this process in the following way: extract reflection data associated with the most prominent feature in the response, work out what this is in terms of change in impedance and amplitude and using the simple waveguide model work out possible interpretations of this first response;

a. input these possible interpretations into the probabilistic model or models being used so each possible interpretation has a probability associated with it;

b. reprocess the live data extracting the next most prominent feature from the data response and do the same for each recognisable feature in the response, what could it be and how likely is this to be true;

c. add each level of processing to the probability model to form a matrix of possible interpretations, with a weighting as to which is most likely to be correct;

d. determine when all recognisable features are detected, and from processing to this point, a most probable interpretation will have been generated, and, based on whether there are several likely solutions or one clear answer a confidence level on the solution will also have been generated.

In this way the complex responses from a well bore sensor wire system can be deciphered and converted into a complete image of fluids over the length of the sensor cable regardless of how complex the fluid regimes are within the well bore.

The probabilistic model used by the processor unit can be developed using one of a number of techniques or any combination mechanisms such as development of a probability tree, a Bayesian belief network or a weighted factor decision rule.

In a probability tree mechanism, the cause of any reflection may be assessed using a probabilistic approach, referred to herein as probabilistic interpretation tree. Software can be used to develop the probabilistic interpretation tree by developing a system wherein a root node is considered to have probability 1.0 and starting from the first reflection in time, and then iteratively all subsequent reflections, all possible interpretations of the source of that reflection are enumerated. Sources of reflections in the well bore example above will include fluid interfaces, known features of the cable such as markers and imperfections, interactions with the liner, and the terminating impedance. For each possible reflection source of the previous part assign a probability so that the sums of such probabilities equals 1.0. This probability to be computed using all previously known information such as time of flight in the various fluids, expected multiple reflections and the expected amplitude of reflections as predicted by the theoretical model. Each such reflection point becomes a child of the previous node of the probabilistic interpretation tree, connected to the previous node (parent) by an edge.

Each child represents a choice of a previously unknown parameter of the theoretical model above. At points in this process, either all points or selected points, a simulation of the expected waveform may be used to further disambiguate choices by conducting a comparison of experimental and theoretical waveform. Such disambiguation may be couched in terms of probabilities of each parent to child edge.

This process is continued until all points of reflection have been processed and the product of the probabilities from the root node to each leaf node of the probabilistic interpretation tree then becomes the probability of the interpretation represented by the path from root to leaf. The path, or paths, with highest probabilities then becomes the interpretation, or most likely candidate interpretations. As paths are built those with very low likelihood may be pruned to improve the efficiency of the algorithm.

An alternative method of developing the probabilistic model is to construct a Bayesian belief network which calculates the probabilities of outcomes using prior information and probabilistic descriptions of interdependencies in the data.

Standard software packages may be used to construct a Bayesian belief network which comprises a set of nodes connected as a directed graph. Dependencies between nodes are indicated by arrows. Nodes may contain discrete information, such as alternative reflection types, or continuously varying information such as a pressure or temperature measurement.

Associated with each node is a table of conditional probabilities expressing the probability of occurrence of any of the states of the node once the states of the nodes on which it depends are known. The first layer nodes are prior information, and contain all that is known in advance about the effect of the well on the pulses. The absence of information is shown by zero probability. Certainty is shown by probability one.

The probabilities of occurrence of each the node states is found by applying Bayes Rule starting from the prior distributions. From this, the state with the largest probability of occurrence can be found.

A yet further method of developing the probabilistic model involves using weighted factor decision rules. Again, standard software packages may be used and a set of attributes which associated with an echo are defined. A possible list is of attributes in this example may include: sign of echo (polarity); arrival time; height; relative height; changes between observations are consistent with change in termination or with same termination.

In addition, a list of echo types is compiled. A possible list includes: termination; marker high to low impedance and fluid high to low impedance.

For each echo type, for each attribute, the range of values of the attribute which apply are defined. For example, the sign of the echo from a high to impedance marker is positive. This results in a list of attributes for each echo type. The attributes of the observed echoes are then listed. The observed attributes are compared with each defined list to select the echo type which most closely matches the observed attributes.

It is further possible to develop the probabilistic model to include modelling of multiple reflections and rebounds. The response of a sensor wire based system is a history of what has happened to the injected pulse as it travels along the sensor wire. Because at every change in the properties of the sensor wire the injected signal is partly transmitted on and party reflected, there are at any given time pulses of varying amplitudes and polarities travelling in different directions. The response which we measure is a series of responses which have been reflected back to the source point. These responses may have come directly from a reflection point, or may be one of a repeating series of responses generated by a partial signal rebounding back and forth between two changes in sensor wire characteristics.

The path which a pulse follows can be characterized as a sequence of directions. Associating forwards travel with a binary '1' or '0' and backwards with a binary '0' or '1', a path can be associated with a binary number. Not all binary numbers are associated with a pulse path. Adopting the convention that forward travel is associated with '1', and that the first is the left most bit, the following conditions are satisfied if a binary number represents the path of a pulse returning to the source.

The first bit is '1' since the pulse travels forward from the source.

The last bit is '0' since the pulse travels backwards on leaving.

The difference between the numbers of '0's' and '1's' must always be greater than or equal to zero and less than or equal to the number of sections.

In association with pulse speed, section length resistive loss and characteristic impedance, for each section, a pulse path defined by a set of directions defines arrival time, boundary interaction loss and total resistive loss If the measurement is taken at the termination, the first arrival travels once through each section. Later arrivals travel three times through adjacent sections before reaching the termination. To represent such a path:—The first bit is '1'. The last bit is '1'. The difference between the numbers of '0's' and '1's' must always be greater than or equal to zero and less than or equal to the number of sections.

It will be appreciated that in another embodiment, the system can implement a mechanism which involves use of time as a variable for producing further response data which can be used by processor unit to establish suitable output data relating to fluid composition. The use of a temporal variable technique requires the processing unit to act upon on a number of time separated response samples, whereby further processing is applied to this series of time separated response readings.

Time variable response readings would be generated by inputting more than one signal into the cable 24, with each signal separated from the subsequent signal by a predetermined and/or known period of time.

This processing of time separated response data comprise injecting a pulse or pulse stream into the cable and iteratively determining the most likely interpretation in terms of fluid mixture changes over the length of the sensor wire. Build a matrix of N readings separated in time with a known absolute sample time, each reading containing a number of possible interpretations, as is consistent with the process outlined above. It will be appreciated that fluid velocity information can optionally be used in processing of the recorded data.

Using this process, a series of readings which exist in a short time interval which share the same probability tree perform pattern matching on consecutive readings can be used in direct comparison or by using correlation techniques to determine if there are any fluid "objects" travelling along the sensor wire, such as slugs, bubbles and solids.

Similarly, using this process, a series of readings which exist in a long time interval which share the same probability tree perform pattern matching on consecutive readings can be used for direct comparison or correlation techniques to determine if there are any fluid changes such as levels moving, increasing presence of bubbles, or foams, increasing or decreasing turbulence.

Using a temporally separated input technique, and then attempting time correlation between samples on different trees or interpretation possibilities the probability of any particular interpretation being correct can be updated, such that interpretations which look probable on a single sample basis but do not make sense on a sample to sample basis will be graded as less likely and visa versa.

This method of temporally separated input data can be used to obtain not only a snap shot of the fluid mixtures in a well bore but also a real time moving analysis in both short and long term movement of the fluids present.

By having fluid flow information available, added knowledge of the fluid velocity would allow the correlation process to be applied in a more focussed manner, making it possible to determine where any given mix or type of fluid "should be" within a well bore based on velocity information in combination with fluid mix data. Such data can be used to estimate the dynamic nature of moving fluids, flowing regimes, and slow changing levels.

The data output from the system using any of the above techniques can result in the provision of a continuous mixture map of a well where the fluid is a changing mixed fluid flow.

Figure 3:
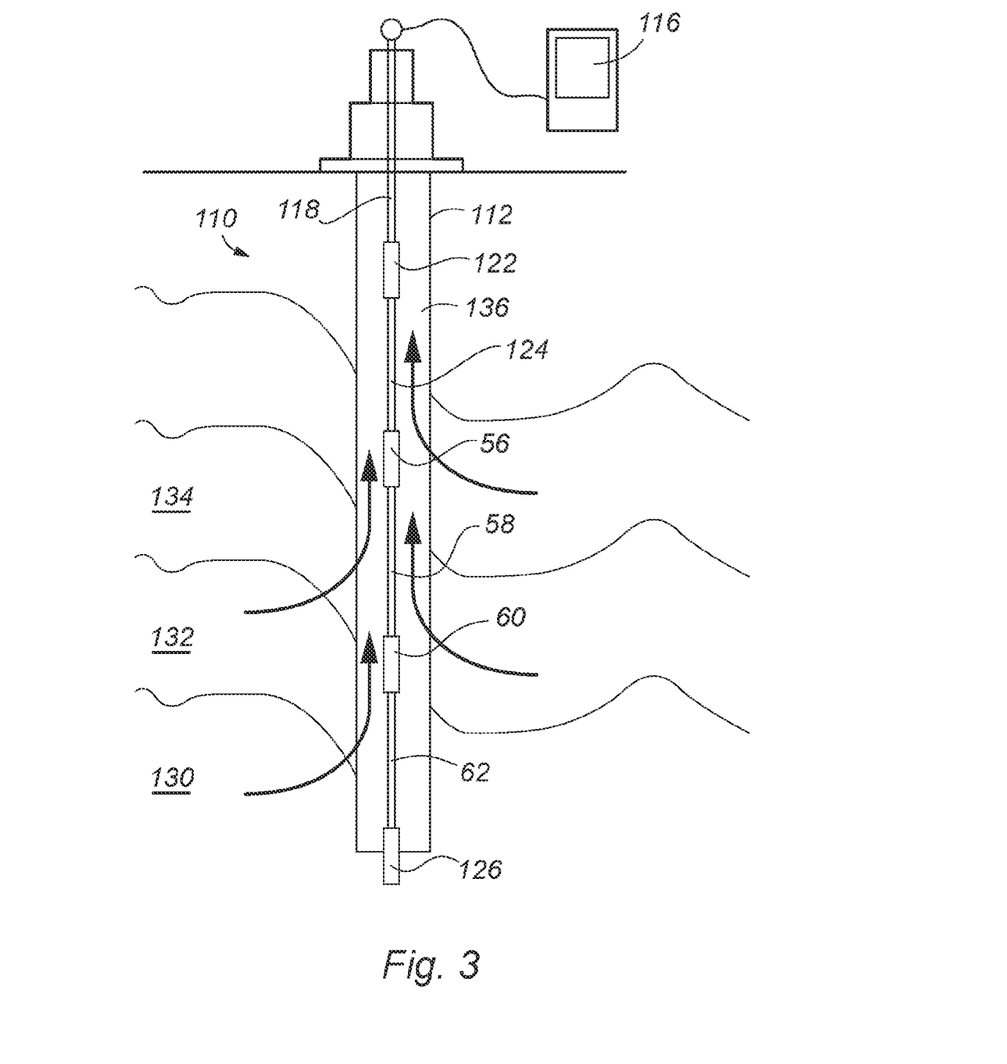
FIG. 3 is a schematic illustration of a fluid measurement system according to a second embodiment of the present invention.

Reference is now made to FIG. 3 of the drawings which illustrates a fluid measurement system, generally indicated by reference numeral 110, according to a further embodiment of the present invention. Like parts to those of FIG. 1 have been given the same reference numeral with the addition of 100 to aid clarity. The fluid measurement system 110 has a processor based surface panel 116 connected to a connecting cable 118 which connects to the sensing sections. The cable 118 connects to an upper electronics module 122, a first sensor wire 124, a second electronics module 56, a second sensor wire 58, a third electronics module 60, a third sensor wire 62 and completed with a lower electronics module 126. While three sensor wires 124,58,62 with electronic modules at either end, any number of zones can be created by selecting the number and length of sensor wires desired.

The sensor wires 124,58,62 are immersed in the well bore 112 with fluids and gasses 130,132,134 all contributing to the well bore fluid mixture 136. The system 110 enables each module 122, 56 and 126 to output a pulse signal and each module is then operable to acquire the response from sensor wire sections 124, 58 and 62 respectively. Determination of the fluid mixture in each zone between the modules can then be carried out by processing the responses using the mechanism detailed above with reference to FIG. 1.

In another embodiment detailed with reference to FIG. 3, down-hole electronics are located in modules 56, 60 can act upon the wire 58, 62 respectively to alter the termination resistances at the cable ends to create known variations in response in each section thus generating known variations in the responses detected.

Figure 4:
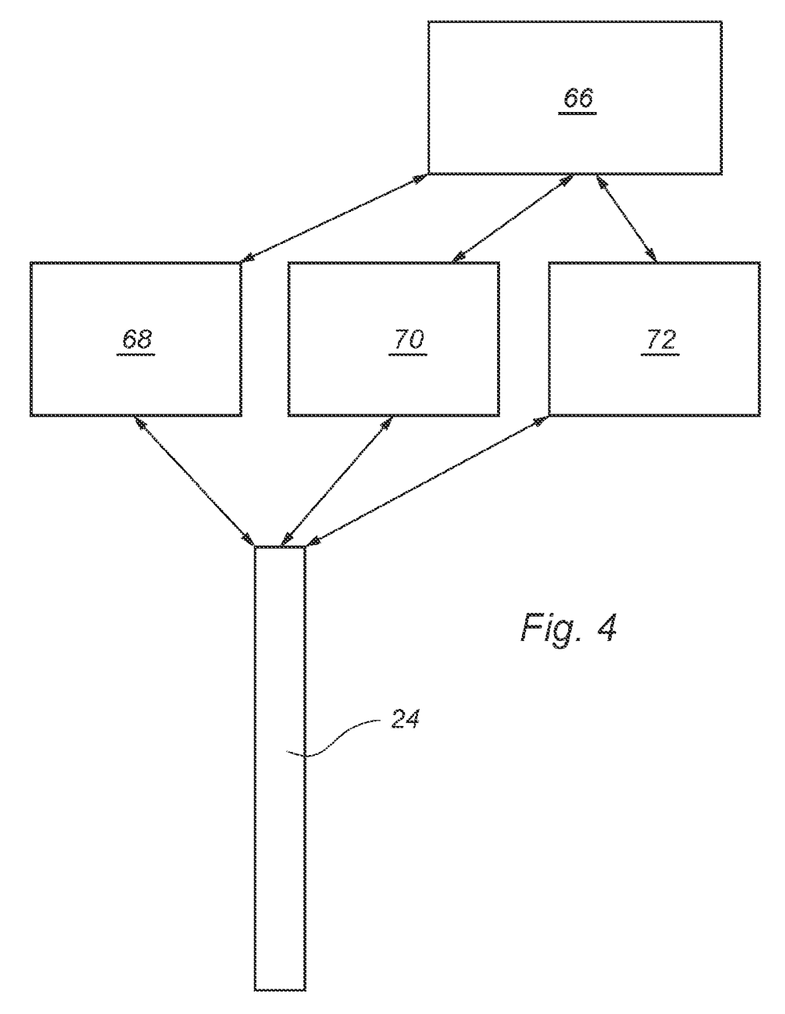
FIG. 4 is a schematic illustration of an electronics module according to an embodiment of the present invention.

The electronics module 22 required to make the measurements detailed with reference to FIGS. 1 and 3 is illustrated in FIG. 4. This includes a processor or embedded PC type device 66, a pulse generator 68, a frequency generator 70 and a high speed data capture module 72, all connected to the sensor wire 24. The electronics module 22 will typically generate a single pulse or pulse stream or pulse sequence. This can be a single pulse or a continuous stream of high frequency pulses. The electronics module may also generate swept sine wave outputs and measure frequency response behaviour as well as reflective behaviour from HF pulses. The processor module 66 may also perform correlation between generated pulse sequences and all recorded responses to achieve highly sensitive out of responses that match the transmitted pulse stream. The pulses may also be coded, for example by using PN sequencing, to remove spurious signals created by reflections from other surfaces in the well bore 12, or noise from surface electrical equipment and the like.

Figure 5:
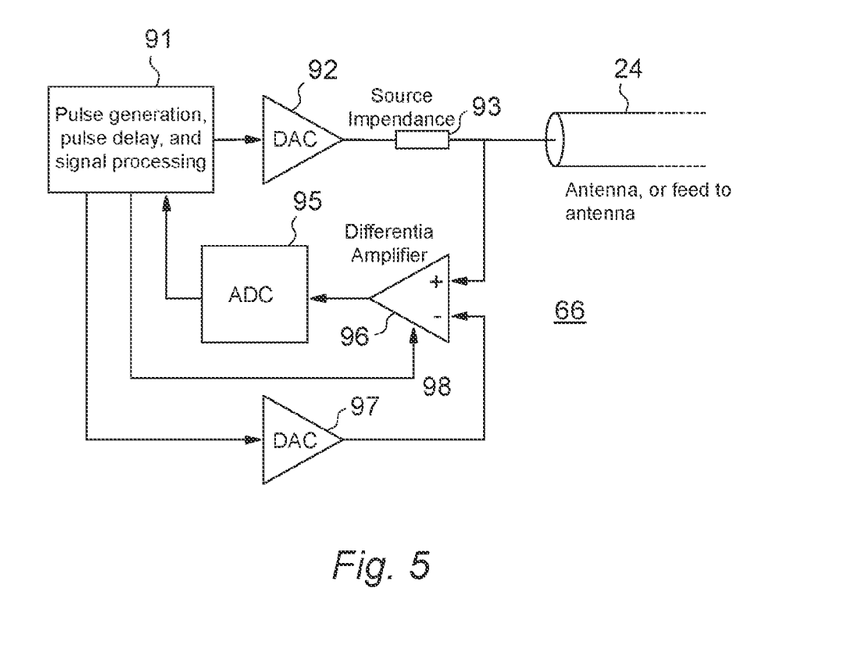
FIG. 5 is a schematic illustration of a signal recovery electronics module according to an embodiment of the present invention.

In FIG. 5 there is shown the data acquisition and processor module 66 of module 22 which enables utilisation of response signals from the cable 24. Part 91 consists of signal generation, delay and processing electronics and will be connected to signal processors such as DSPs and/or FPGAs. Part 91 will generate the digital representation of the waveform to be transmitted to the sensing cable 24, either directly, or by way of a feed cable (not shown) via the DAC 92 and the source impedance 93.

Differential amplifier 96 is high bandwidth and has high linearity criteria which are selected despite a potential cost in terms of the gain which may be achieved. The gain of the differential amplifier 96 is controlled by part 91 via the connection 98. This differential amplifier 96 subtracts from the received signal a second signal generated by part 91 in digital format and converted to analogue by part 97, a second DAC.

During operation, Part 91 repeats of a process of identifying the signal of greatest magnitude at the output of the ADC 95; generating a signal of equal magnitude and apply this to the subtracting input of the differential amplifier 96 and increasing the gain of the differential amplifier 96 to make full use of the dynamic range of the ADC. Repetition of this process allows, for a stationary response, weaker signals to be identified. For a non-stationary cable techniques generally known as adaptive signal processing may be applied to achieve the same effect.

In known prior art arrangements, the use of pseudo-noise or other waveforms with cross-correlation properties similar to pseudo-noise sequences, as typified by CDMA communications systems, is limited by the so called "near-far" problem. This arises when the signal received consists of large and small signals, and due to imperfections in the receiver construction, such as non-linearities and limited dynamic range in A/Ds, recovery of the small signals is severely limited. In the systems of FIGS. 1 and 3, using time domain reflectometry down-hole, a similar situation arises with large reflections from nearby features giving rise to strong signals, and reflections from distant features typically, largely as a result of attenuation, give rise to weak signals.

The module 66 alleviates this problem by the utilising the knowledge of the transmitted waveform such that the delayed and distorted returned waveform, is already known at the transmitter upon transmission. Thus, the returned signal will consist of strong reflections from nearby artefacts, and weak reflections from small or far away artefacts.

Due to limitations of the analogue to digital converter (ADC) 95 (or if correlation is carried out in the analogue domain, non-linearities within multipliers), the weak signal (s) will not be recoverable if they fall beneath the noise floor of the ADC.

However, using the module 66, as all returned signals arise from delayed and/or linearly modified versions of the transmitted signal once the strong signals have been identified by the signal processing part 91, those strong signals are subtracted from the returned signal, thus reducing the dynamic range of the signal passed to the ADC 95 and therefore enabling higher amplification of the remaining signal before analogue to digital conversion. As a result, weak signals within the response may now be identified.

Figure 6:
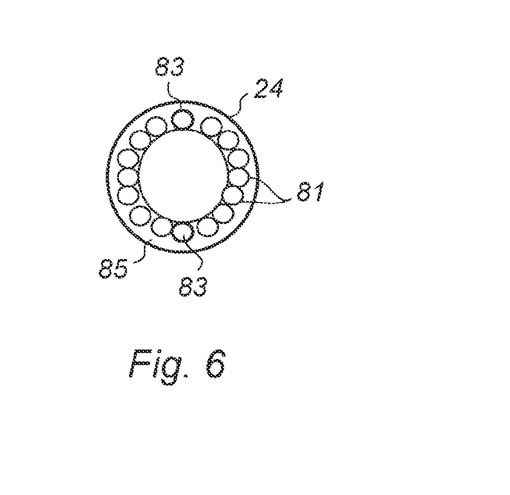
FIG. 6 is a cross section of a cable for use in the present invention.

Within the embodiments of the above system, the sensing cable 24 capable of withstanding the rigors of a down-hole environment is required. With reference to FIG. 6 there is shown an embodiment of a cross section of sensing cable 24 which utilises low dielectric constant material and/or low attenuation core material 81 within an outer material 85 able to withstand down-hole use. Conductors 85 have a circular cross section which is an advantage for manufacturing purposes however it will be understood that the cables may be formed having other cross sectional shapes such as square, rectangular, triangular, elliptical, oval, and hexagonal.

It will be further appreciated that conductors 85 constructing the transmission line may also be multiple rather than the single conductors. In this way, a parallel set of sensor wires can be arranged to provide multiple responses through the same volume of fluid. The wires can be twisted to form a spiral so that the effective length for the pulses to travel is greater than the physical length of the wire. Each sensor wire in the set may be terminated at a different length which will give comparative responses over varying lengths. Additionally, the sensor wires could be arranged from a main branch wire.

It will be appreciated that conductors 85 may be embedded (not shown) within the low dielectric constant material 83 such as, but not limited to polypropylene, air (where ambient pressure permits), and commercial compounds such as Nylon, PVDF and other mixtures of plastic and insulating materials.

The principle advantage of the present invention is that it provides a system and method of measuring the fluid type and mixture present in over a length of a well bore in which fluid is flowing.

A further advantage of the present invention is that it can make the determination in near real-time allowing for improved efficiency in operating a well.

A yet further advantage of the present invention is that it can make the determination on a producing well without the requirement of stopping production during measurement as with prior art logging systems.

It will be apparent to those skilled in the art that modifications may be made to the invention herein described without departing from the scope thereof. For example, while the Figure show vertical well bores, the system can be run through any conduit in any orientation. This horizontal and multi-lateral well bores can be used. Additionally the system finds application in pipelines. Furthermore the sensor wire detailed may be provided with or without characteristic impedance markers so that it covers the part of the well bore where fluid mixtures can change, or indeed over any area of interest.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A fluid measurement system comprising:
    an elongate member for location in a well bore;
    a signal generator for injecting a high frequency signal along the member;
    a data acquisition unit to record first reflected signals received from the member;
    a system criteria unit to maintain a data set relevant to the system, wherein the data set comprises a model of one or more fluid interfaces; and
    a processor unit operable to act upon the first reflected signals and the data set to establish an output indicative of component fluid within the well bore from which the mixture of fluids flowing within the well bore can be determined.
2. The fluid measurement system according to claim 1, wherein the processor acts upon one or more of a set of response characteristics from a set comprising: signal velocity, signal group and signal phase.
3. The fluid measurement system according to claim 1, wherein the signal generator provides a signal selected from a group comprising: modulated carriers, pulse streams, pulse sequences, pulse bursts and a PN sequence of high frequency pulses.
4. The fluid measurement system according to claim 1, wherein the signal generator is operable to apply a second high frequency signal to the member and the data acquisition unit is operable to record second reflected signals received from the member; wherein the processor unit is operable to act upon the first reflected signals, second reflected signals and the data set to establish an output indicative of component fluid within the well bore from which the mixture of fluids flowing within the well bore can be determined.
5. The fluid measurement system according to claim 4, wherein the first signal and second signal are different signals.
6. The fluid measurement system according to claim 4 wherein the first and second signals are identical signals and an alternative known differential is applied to the system during the injection of one of the first signal and the second signal, wherein the alternative known differential enables the first and the second signals to be distinguished from one another.
7. The fluid measurement system according to claim 6, wherein the known differential is a time delay occurring between the first signal and second signal being applied to the member.
8. The fluid measurement system according to claim 7, wherein the member is provided with at least one adaptive unit.
9. The fluid measurement system according to claim 8, wherein the adaptive unit alters at least one characteristic of the member.
10. The fluid measurement system according to claim 9, wherein the system further comprises a plurality of signal generators located along the length of the member each having an associated data acquisition unit, each signal generator operable to inject signals into a section of the member.
11. The fluid measurement system according to claim 10, wherein the system criteria unit data set includes at least one of a mathematical model of the well bore; a model of multiple fluid interfaces and multiple reflections from these fluid changes based on waveguide theory; dielectric property of fluids data; well bore environment data; an iteratively generated model of relevant environmental factors and a probabilistic model of possible fluid regimes.
12. A method of determining a fluid mixture flowing in a conduit, the method comprising:
    locating a first cable through a length of the conduit;

injecting a first high frequency signal along the cable and injecting a second high frequency signal to the cable;

recording a first response of reflected signals from the cable;

recording a second response of reflected signals from the cable;

utilising known conduit criteria and the first and/or second reflected signals to establish fluid characteristics; and determining a mixture of fluids flowing through the length of the conduit using the established fluid characteristics.

13. The method of determining fluid mixture according to claim 12, wherein the method is an iterative process with the steps being repeated.

14. The method of determining fluid mixture according to claim 12, wherein injecting a first high frequency signal along the cable further comprises injecting the second high frequency signal to the cable at a predetermined time period after the first high frequency signal is injected to the cable.

15. The method of determining fluid mixture according to claim 14, wherein injecting a first high frequency signal along the cable further comprises adapting the cable after the injection of the first signal to create known variations in response such that the first response and the second response are distinguishable from one another.

16. The method of determining fluid mixture according to claim 12, wherein injecting a first high frequency signal along the cable comprises injecting a PN sequence of high frequency pulses and recording a first response of reflected signals from the cable includes matching the correct pulse sequence to record a response.

17. The method of determining fluid mixture according to claim 12, wherein utilising known conduit criteria and the first reflected signals to establish fluid characteristics includes the step of comparing the response to a predetermined data set.

18. The method of determining fluid mixture according to claim 17, wherein the predetermined data set is a mathematical model.

19. The method of determining fluid mixture according to claim 12, wherein the known conduit criteria of utilising known conduit criteria and the first reflected signals to establish fluid characteristics is an existing recorded response.

20. The method of determining fluid mixture according to claim 12, wherein the method further includes the step of measuring responses at a plurality of locations along the cable.

* * * * *